US00PP17095P2

(12) United States Plant Patent
Riordan

(10) Patent No.: US PP17,095 P2
(45) Date of Patent: Sep. 12, 2006

(54) ST. AUGUSTINEGRASS NAMED 'TR 6-10'

(50) Latin Name: *Stenataphrum secundatum*
Varietal Denomination: TR 6-10

(76) Inventor: Terrance P. Riordan, 6608 Old Domininon Rd., Lincoln, NE (US) 68516

( * ) Notice: Subject to any disclaimer, the term of this patent is extended or adjusted under 35 U.S.C. 154(b) by 4 days.

(21) Appl. No.: 10/922,234

(22) Filed: Aug. 19, 2004

(51) Int. Cl.
*A01H 5/00* (2006.01)

(52) U.S. Cl. ..... Plt./392
(58) Field of Classification Search ..... Plt./392
See application file for complete search history.

(56) References Cited

PUBLICATIONS

SNA Research Conference—vol. 41–1996. Section 10 Landscape. Robert Harris Section Editor. pp. 265, 297–299.*

* cited by examiner

*Primary Examiner*—Kent Bell
*Assistant Examiner*—Annette H Para
(74) *Attorney, Agent, or Firm*—Suiter West Swantz pc llo

(57) ABSTRACT

St. Augustinegrass 'TR 6-10' is a perennial St. Augustinegrass cultivar with dwarf turfgrass characteristics. 'TR 6-10' is a bright, dark green color and yet exhibits a dwarf, low growing habit. It is more wear tolerant than other St. Augustinegrasses and it is the most shade tolerant cultivar of a species that is highly regarded for this characteristic.

5 Drawing Sheets

BACKGROUND OF THE INVENTION

St. Augustinegrass [*Stenataphrum secundatum* (Walt) Kuntze] is a perennial, low growing warm-season species adapted to Florida, Texas and other southern areas where freezing temperatures are not a severe annual problem. It thrives on sandy and heavy soils where adequate moisture is available. Common St. Augustinegrass is coarse textured, spreads by stolons and roots at each node that comes in touch with the soil. Its inflorescence is a spike that is usually found terminally on a stolon. Florets are fertile or sterile and the fertile floret produces male and female flowers whose color can often be used to help identify individual cultivars.

SUMMARY OF THE INVENTION

This invention is regarding a new and distinct perennial St. Augustinegrass variety intended for use in turfgrass situations. This genotype was developed under a research contract in the research greenhouses at the University of Nebraska, Lincoln, from a cross between two clones of St. Augustinegrass that had multiple outstanding traits. Cultivar 'TR 6-10' has been evaluated for a number of years in multiple locations and it was selected because of its excellent performance, tolerance to a number of pest problems, and specific traits of this turfgrass species. This plant exhibits its dwarf characteristics including shorter and narrower leaves than other St. Augustinegrass cultivars. These characteristics create a very attractive turf and will allow 'TR 6-10' to be distinguished from other cultivars of St. Augustinegrass.

BRIEF DESCRIPTION OF THE DRAWINGS

The numerous advantages of the present invention may be better understood by those skilled in the art by reference to the accompanying figures in which.

DETAILED BOTANICAL DESCRIPTION OF THE INVENTION

St. Augustinegrass 'TR 6-10' ('TR 6-10') was bred from a cross between two experimental clones of St. Augustinegrass that had multiple outstanding characteristics. These parents were genotypes generated from crosses of selections with excellent turf quality and excellent cold tolerance. 'TR 6-10' has a gross morphology similar to each of the parents (and to St. Augustinegrasses), but it only has some of the characteristics of each of these parents. After being bred it was vegetatively (asexually) propagated. St. Augustinegrass is a cross pollinated species that is capable of self pollinating. In particular, 'TR 6-10' was propagated vegetatively (asexually) at the Scotts Company Cleveland, Tex. research facility. Stolons and plugs were used to propagate the 'TR 6-10' cultivar. The 'TR 6-10' cultivar is completely stably reproduced by the aforementioned vegetative propagation (asexually). The morphological characteristics, molecular characteristics, and turfgrass evaluation ratings may be used to distinguish 'TR 6-10' from other commercially produced St. Augustinegrass varieties.

Morphological Characteristics

Figure 1:
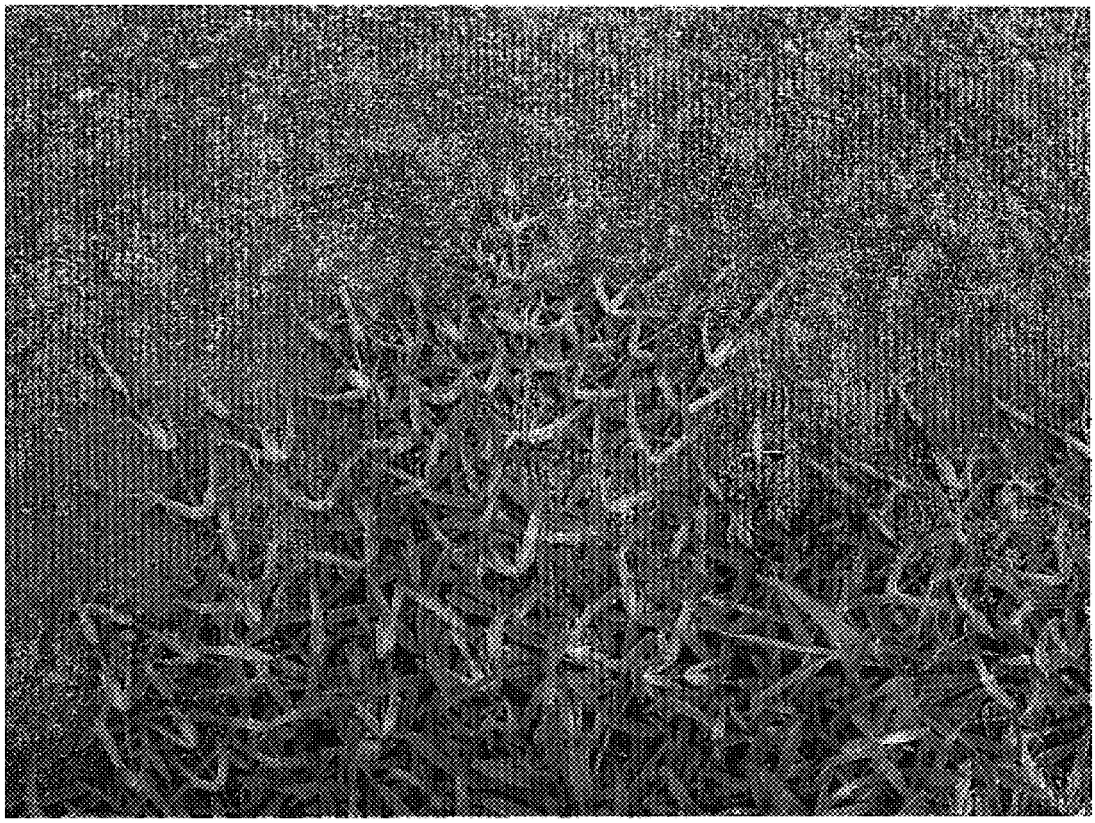
FIG. 1 is a photograph illustrating a section of turf produced by a typical stolon field of a St. Augustinegrass 'TR 6-10' in accordance with an exemplary embodiment of the present invention.
Figure 2:
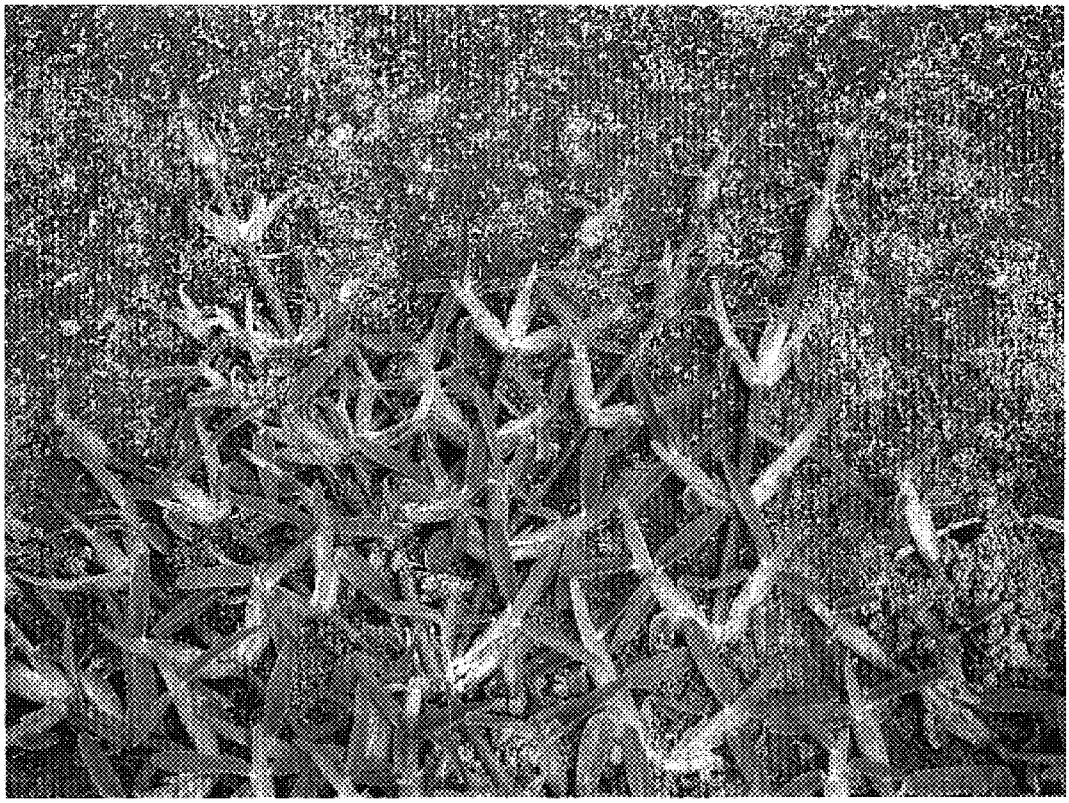
FIG. 2 is a photograph providing an expanded view illustrating the section of turf produced by the stolon field of the St. Augustinegrass 'TR 6-10' in accordance with an exemplary embodiment of the present invention.

Referring generally to FIGS. 1 through 5, St. Augustinegrass 'TR 6-10' ('TR 6-10') exhibits dwarf cultivar characteristics. A comparison of 'TR 6-10' with '6-89-196', '6-89-175', Delmar, Floratam, and Seville was conducted. Tables 1 and 2 show that 'TR 6-10' exhibits shorter stolons and internodes, characteristic of a dwarf cultivar, which distinguishes it from '6-89-196' and '6-89-175'. Further, Tables 1 and 2 illustrate that the leaves of 'TR 6-10' are shorter and narrower than the Delmar, Floratam, and Sevile. With this leaf structure, 'TR 6-10' exhibits a finer texture of leaf than Delmar, Floratam, and Seville as measured by leaf and density characteristics, which will be discussed herein below. 'TR 6-10' also has fewer stolons and a shorter average internode length when compared to the other cultivars. The combination of these characteristics, and others described herein below, results in fine turf quality and texture, as illustrated in FIG. 1.

'TR 6-10' is coarse textured, spreads by branching stolons and forms a dense, spongy turf. 'TR 6-10' is adapted to warmer climates of the United States where low temperatures and frost are not usual. 'TR 6-10' has a ligule consisting of a very short fringe of hairs. The vernation is folded, there are no auricles and the collar is broad, continuous and narrowed at the base of the leaf. There are a number of leaf hairs in the collar area. The 'TR 6-10' leaf blade is flat, smooth and has a blunt tip. The inflorescence is a spike. These characteristics are very similar to all other St. Augustinegrasses and can be used to identify the species, but can not be used to distinguish 'TR 6-10' from other St. Augustinegrasses genotypes.

'TR 6-10' is different and can be identified as different from its two parents and all other St. Augustinegrasses because of the characteristic, shade tolerance. St. Augustinegrass is known for having excellent shade tolerance, but 'TR 6-10' far exceeds any other St. Augustinegrass in its ability to grow under low light conditions (see below, Table 11). None of the selections that were the parents or grandparents of 'TR 6-10' have been identified as having shade tolerance better than other St. Augustinegrass selections.

TABLE 1

Leaf and stolen measurements from greenhouse evaluations.

| Selection | Leaf Length cm | Leaf Width cm | Internode length cm |
|---|---|---|---|
| TR 6-10 | 2.3 | 0.56 | 3.37 |
| 6-89-196 | 2.0 | 0.48 | 2.56 |
| 6-89-175 | 1.9 | 0.53 | 3.89 |
| Delmar | 5.1 | 0.77 | 3.52 |
| Floratam | 5.9 | 0.71 | 6.66 |
| Seville | 3.8 | 0.58 | 5.16 |
| LSD | 0.8 | 0.07 | 0.70 |

TABLE 2

Stolen measurements from greenhouse evaluations.

| Selection | Stolon # | Stolon Length cm |
|---|---|---|
| TR 6-10 | 3.8 | 23.9 |
| 6-89-196 | 6.8 | 24.6 |
| 6-89-175 | 10.2 | 41.2 |
| Delmar | 7.5 | 20.6 |

TABLE 2-continued

Stolen measurements from greenhouse evaluations.

| Selection | Stolon # | Stolon Length cm |
|---|---|---|
| Floratam | 8.3 | 48.1 |
| Seville | 17.5 | 47.7 |
| LSD | 3.0 | 10.3 |

Molecular Characteristics

Flow cytometry is a rapid way to differentiate between varieties having different numbers of chromosomes, and sometimes can differentiate among varieties having the same number of chromosomes. DNA contents of various St. Augustinegrass cultivars including 'TR 6-10', 6-89-196, 6-89-175, Delmar, and Floratam were determined. Using flow cytometry following standard protocols (Arumuganathan & Earle, 1991; Johnson, Riordan & Arumuganathan, 1998) with two runs of each St. Augustinegrass, a comparison study was performed. It was found that the DNA content of 'TR 6-10' is similar to Delmar. Comparing this to chromosome counts reported in the '6-72-182' patent document where Floratam is recorded with 27 chromosomes and Delmar with 18 chromosomes (Mixson, Riordan & Meier, 1989), 'TR 6-10' is an 18 chromosome type cultivar, shown in Table 3 below.

TABLE 3

DNA content and inferred chromosome number of St. Augustinegrass cultivars.

| Selection | DNA content Pg DNA/nucleus | Chromosome Number |
|---|---|---|
| 'TR 6-10' | 1.16 | 18 |
| 6-89-196 | 1.15 | 18 |
| 6-89-175 | 1.17 | 18 |
| Delmar | 1.14 | 18 |
| Floratam | 2.29 | 27 |

Turfgrass Characteristics

Turfgrass quality may be established using a combination of several factors, such as color, texture, density, and uniformity. Based on color measurements alone, St. Augustinegrass 'TR 6-10' is similar to Seville, Floratam, and Delmar using cluster analysis (Table 4). 'TR 6-10' is a brighter green than the cultivars exhibited in '6-89-196' and '6-89-175'. Color measurements were made using a Minolta CR-200 chromometer. Color measurements were interpreted in accordance with standard color charting principles (McGuire, 1992).

TABLE 4

Color measurements from greenhouse evaluations.

| Selection | Chroma C† | L‡ |
|---|---|---|
| TR 6-10 | 27.84 | 47.10 |
| 6-89-196 | 22.51 | 42.16 |
| 6-89-175 | 26.12 | 45.88 |
| Delmar | 30.52 | 45.14 |
| Floratam | 30.24 | 48.46 |
| Seville | 31.93 | 45.19 |
| LSD | 2.35 | 1.97 |

TABLE 4-continued

Color measurements from greenhouse evaluations.

| Selection | Chroma C† | L‡ |
|---|---|---|

†Color saturation. Lower values equate greater saturation.
‡'L' measures lightness and darkness. A high 'L' value indicated a light color (light green) and a low 'L' value indicates darker colors (dark green).

'TR 6-10' has an excellent dark green leaf color and this characteristic can be used to separate it from Raleigh in the field (Table 5). As seen in Table 5, from a color comparison with Floratam, Bitterblue, Seville, and Delmar cultivars, the color of 'TR 6-10' may be similar to these other St. Augustinegrass cultivars. The dark green leaf color of 'TR 6-10' is an excellent color for a turfgrass being used in a residential setting.

TABLE 5

Genetic Color Ratings of St. Augustinegrass Cultivars - NTEP Data.
Genetic Color Ratings Qualitative Scale for Plant Color 1–9; 1 = Yellow, 5 = Medium Green, 9 = Dark Green.

| Name | FL2 | FL3 | FL4 | FL5 | SC1 | TX3 | Mean |
|---|---|---|---|---|---|---|---|
| Floratam | 6.7 | 7.7 | 7.0 | 8.7 | 5.0 | 7.0 | 7.0 |
| TR 6-10 (DD-11) | 6.7 | 8.3 | 8.3 | 4.7 | 5.0 | 8.0 | 6.8 |
| Bitterblue | 6.7 | 7.7 | 5.7 | 7.7 | 5.0 | 7.0 | 6.6 |
| Seville | 6.0 | 8.3 | 6.3 | 6.7 | 5.0 | 7.3 | 6.6 |
| Delmar | 7.7 | 6.3 | 5.7 | 5.0 | 5.0 | 8.7 | 6.4 |
| Raleigh | 5.0 | 5.7 | 6.7 | 5.7 | 5.0 | 7.3 | 5.9 |
| LSD Value | 1.5 | 1.5 | 3.7 | 1.1 | 0.6 | 0.5 | 0.7 |

To determine statistical differences among entries, subtract one entry's mean from another entry's mean. Statistical differences occur when this value is larger than the corresponding LSD value (LSD 0.05).

Figure 3:
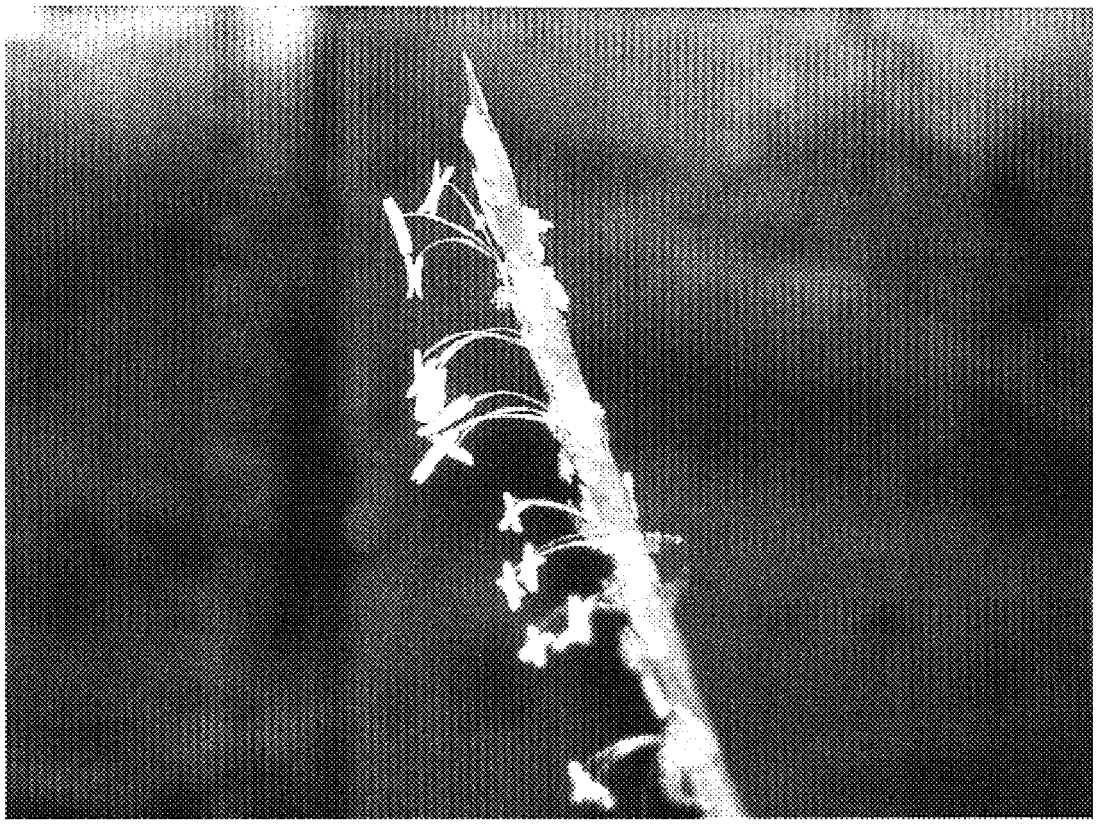
FIG. 3 is a photograph illustrating a typical flower of the St. Augustinegrass 'TR 6-10' in accordance with an exemplary embodiment of the present invention.
Figure 4:
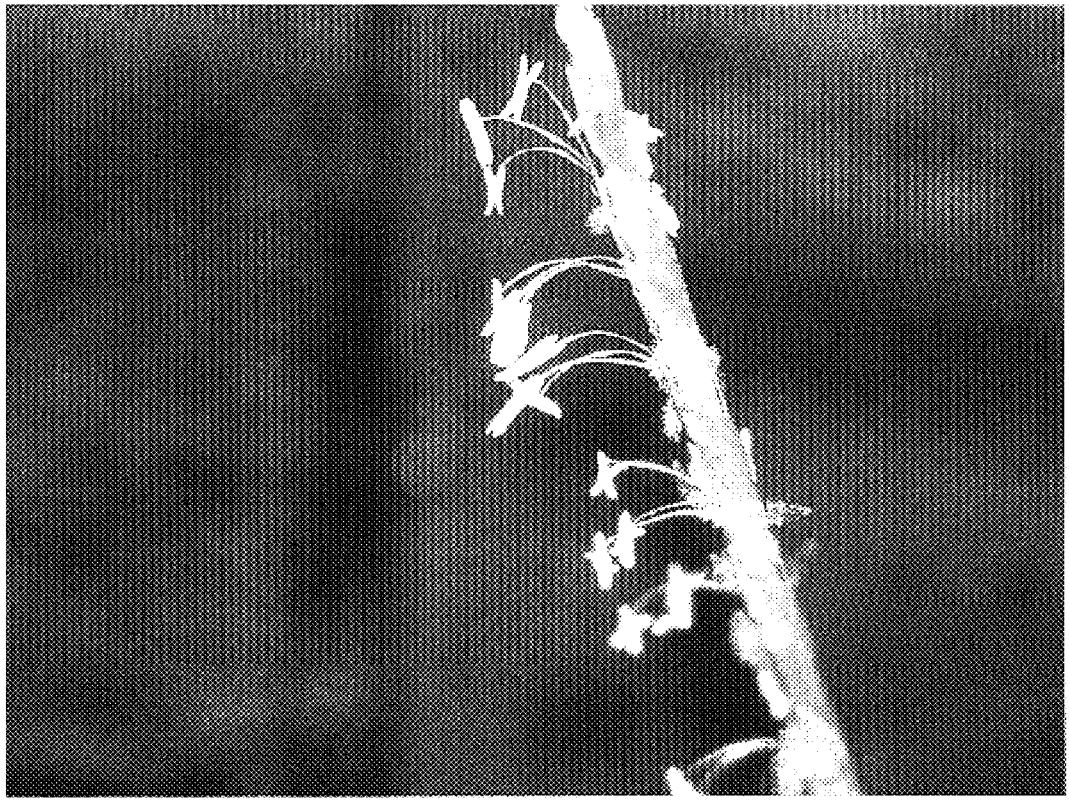
FIG. 4 is a photograph providing an expanded view illustrating the flower of the St. Augustinegrass 'TR 6-10' in accordance with an exemplary embodiment of the present invention.
Figure 5:
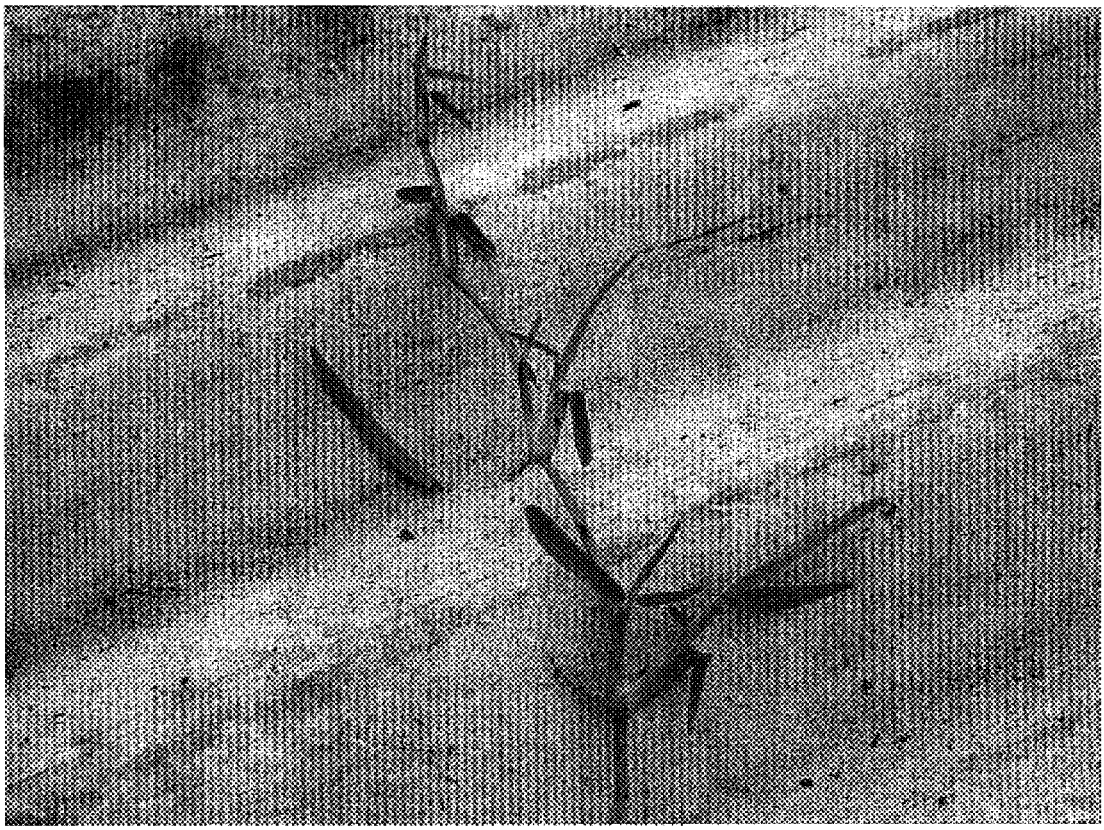
FIG. 5 is a photograph illustrating a typical stolon of the St. Augustinegrass 'TR 6-10' in accordance with an exemplary embodiment of the present invention.

It is contemplated that having markers which may be used to identify hybrids may provide a significant advantage when it comes to the identification of the 'TR 6-10' cultivar. Observations of stigma and anther color in a number of commercially available cultivars indicate that this characteristic (color) is stable and it can be used to identify genotypes. Thus, these color "markers" may be used to identify hybrids. The colors of the stigmas and anthers of 'TR 6-10' are white, purple or yellow, as illustrated in FIGS. 3 and 4. The flower color readings in Table 6 show that the color of the flower of 'TR 6-10' may be used to distinguish it from several other cultivars.

TABLE 6

St. Augustinegrass Cultivar Flower Color.

| Selection | Stigma Color | Anther Color |
|---|---|---|
| TR 6-10 | Light Purple | Light Yellow |
| Texas Common | White | Light Yellow |
| Raleigh | White | Medium Yellow |
| Delmar | White | White |
| Floratam | Deep Purple | Deep Yellow |
| Seville | Light Purple | Light Yellow |
| Gulf Star | Deep Purple | Light Purple |

With its shorter and narrower leaves than the other cultivars, 'TR 6-10' has a very fine leaf texture, as shown in Table 7, and this characteristic may be used to distinguish it from other standard cultivars. The fine leaf texture provides 'TR 6-10' with an excellent appearance. The only cultivar that has a leaf texture similar to 'TR 6-10' is Seville. As previously stated, the fine leaf texture, density, and uniformity of growth of the 'TR 6-10' cultivar gives 'TR 6-10' multiple desirable turfgrass characteristics.

TABLE 7

Leaf Texture Ratings of St. Augustinegrass Cultivars - NTEP Data.
Leaf Texture Ratings Qualitative Scale for Plant Texture 1–9; 1 = Coarse, 5 = Medium Coarseness, 9 = Very Fine.

| Name | FL2 | SC1 | TX3 | Mean |
|---|---|---|---|---|
| TR 6-10 (DD-11) | 7.3 | 5.7 | 7.7 | 6.9 |
| Seville | 6.7 | 5.3 | 8.3 | 6.8 |
| Raleigh | 5.3 | 4.3 | 7.0 | 5.6 |
| Delmar | 3.7 | 5.0 | 7.3 | 5.3 |
| Bitterblue | 3.0 | 4.0 | 8.3 | 5.3 |
| Floratam | 1.0 | 3.3 | 8.3 | 4.2 |
| LSD Value | 1.6 | 1.1 | 0.9 | 0.7 |

To determine statistical difference among entries, subtract one entry's mean from another entry's mean. Statistical difference occur when this value is larger than the corresponding LSD value (LSD 0.05).

Twenty-five (25) commercially available and experimental St. Augustinegrass cultivars were evaluated for wear tolerance and other associated characteristics (Busey, 1991). 'TR 6-10' was identified because of its shorter internode length, smaller stolon thickness (except Seville), and shorter unmown height (except Seville). 'TR 6-10' is a dwarf cultivar which has a shorter stature than other available St. Augustinegrass cultivars, including the semi-dwarf cultivar, Seville. As shown in Table 8, below, the study revealed that 'TR 6-10' had a wear tolerance better than all 25 commercially available cultivars and experimentals included in the study, which is an important characteristic of turfgrasses.

TABLE 8

Morphological characteristics and wear tolerance ratings of selected St. Augustinegrass cultivars.
Wear Tolerance ratings from 1 to 9; 1 = Poor Wear Tolerance, 5 = Medium Wear Tolerance, 9 = Best Wear Tolerance.

| Cultivar/ Species | Internode Length mm | Stolon Thickness mm | Leaf Blade Thickness mm | Unmown Height cm | Wear Tolerance |
|---|---|---|---|---|---|
| TR 6-10' | 31.6 | 2.21 | 0.203 | 5.1 | 8.8 |
| 'Delmar' | 41.0 | 2.97 | 0.191 | 9.3 | 3.8 |
| 'Raleigh' | 47.2 | 3.08 | 0.201 | 11.8 | 6.9 |
| 'Seville' | 45.2 | 2.50 | 0.209 | 7.3 | 7.0 |
| 'Floratam' | 58.4 | 3.25 | 0.221 | 11.3 | 3.0 |
| M.S.D. (p = 0.05) | 5.7 | 0.26 | 0.016 | 3.7 | 1.0 |

'TR 6-10' was an entry in the 1989 National Turfgrass Evaluation Program St. Augustinegrass trial. 'TR 6-10' was compared to standard cultivars at the time. As shown below in Tables 9 and 10, for the characteristic Turfgrass Quality, 'TR 6-10' performed very well at all locations except at the Texas location at Dallas. At this location low temperatures may have had an effect on the performance of all St. Augustinegrass cultivars. These trials were all in the open sun so that the shade performance ability of 'TR 6-10' was not a factor; however, the excellent performance of 'TR 6-10' may be used to distinguish it from other cultivars.

TABLE 9

Mean Turfgrass Quality Ratings of St. Augustinegrass Cultivars at Seven Locations in the United States - NTEP Data. Selected Turfgrass Quality Ratings 1–9; 1 = Poor, 5 = Medium, 9 = Ideal.

| Name | CA1 | FL2 | FL3 | MS1 | SC1 | TX1 | TX3 | MEAN |
|---|---|---|---|---|---|---|---|---|
| TR 6-10 | 5.8 | 6.7 | 8.7 | 6.6 | 6.0 | 2.5 | 7.3 | 6.2 |
| Seville | 5.5 | 6.7 | 8.4 | 6.7 | 5.0 | 3.9 | 7.0 | 6.2 |
| Bitterblue | 5.7 | 7.3 | 8.1 | 5.2 | 4.3 | 3.1 | 5.2 | 5.6 |
| Delmar | 5.7 | 7.0 | 7.4 | 5.4 | 4.7 | 2.7 | 5.8 | 5.5 |
| Floratam | 4.8 | 6.0 | 6.4 | 5.8 | 5.0 | 3.6 | 5.2 | 5.3 |
| LSD Value | 0.9 | 1.8 | 0.9 | 0.9 | 1.1 | 1.6 | 0.5 | 0.4 |

To determine statistical difference among entries, subtract one entry's mean from another entry's mean. Statistical difference occur when this value is larger than the corresponding LSD value (LSD 0.05).

TABLE 10

Mean Turfgrass Quality Ratings of St. Augustinegrass Cultivars for Each Month Grown at Seven Location in the United States - NTEP Data. Selected Turfgrass Quality Ratings 1–9; 1 = Poor, 5 = Medium, 9 = Ideal.

| Name | Jan | Feb | Mar | Apr | May | Jun | Jul |
|---|---|---|---|---|---|---|---|
| TR 6-10 | 2.3 | 5.7 | 6.5 | 4.0 | 5.1 | 6.3 | 7.4 |
| Seville | 2.3 | 5.5 | 6.0 | 4.2 | 5.3 | 6.3 | 7.1 |
| Delmar | 3.3 | 6.3 | 7.2 | 3.2 | 4.3 | 5.5 | 5.8 |
| Floratam | 2.7 | 5.2 | 5.3 | 3.3 | 4.3 | 5.3 | 5.9 |
| Raleigh | 2.5 | 4.7 | 5.2 | 4.2 | 4.8 | 5.3 | 6.0 |
| LSD Value | 1.7 | 2.9 | 2.5 | 2.0 | 1.4 | 1.2 | 1.1 |

| Name | Aug | Sep | Oct | Nov | Dec | Mean |
|---|---|---|---|---|---|---|
| TR 6-10 | 5.8 | 6.4 | 5.7 | 4.3 | 6.8 | 6.2 |
| Seville | 6.6 | 6.6 | 6.4 | 4.7 | 6.5 | 6.2 |
| Delmar | 5.4 | 5.5 | 5.3 | 3.7 | 6.2 | 5.5 |
| Floratam | 5.4 | 5.7 | 5.8 | 4.0 | 5.5 | 5.3 |
| Raleigh | 5.9 | 5.7 | 5.8 | 4.0 | 4.3 | 5.2 |
| LSD Value | 1.3 | 1.2 | 1.4 | 2.6 | 1.1 | 0.9 |

To determine statistical difference among entries, subtract one entry's mean from another entry's mean. Statistical difference occur when this value is larger than the corresponding LSD value (LSD 0.05).

Another important factor in turfgrass quality may be shade tolerance. Shade tolerance and associated characteristics of thirty-one (31) St. Augustinegrass cultivars and experimentals were compared and reported (Leblanc & McCrimmon, 1997), the results of that study for the 'TR 6-10', Delmar, Raleigh, Seville, and Floratam cultivars are shown below in Table 11. In this study 'TR 6-10' was the highest ranked cultivar for percent cover, shoot dry weight, stolon number, total stolon length, and average ranking. Thus, clearly 'TR 6-10' has the ability to thrive and persist under lower light conditions. This ability may be used to distinguish 'TR 6-10' from all other St. Augustinegrass cultivars. The species, St. Augustinegrass, is known to be very shade tolerant, but a cultivar with enhanced shade tolerance, such as that provided by the St. Augustinegrass 'TR 6-10' of the present invention, may allow consumers to have a healthier and better performing lawn under often normal high shade conditions.

TABLE 11

Turfgrass performance under natural tree shade, Rankings for percent cover, shoot dry weight, stolon number, total stolon length, and average ranking.

| Cultivar/ Species | Percent Cover | Shoot Dry Weight | Stolon Number | Total/Stolon Length | Average Ranking |
|---|---|---|---|---|---|
| 'TR 6-10' | 1 | 1 | 1 | 1 | 1.0 |
| 'Delmar' | 4 | 2 | 10 | 13 | 7.3 |
| 'Raleigh' | 10 | 9 | 14 | 12 | 11.3 |
| 'Seville' | 17 | 17 | 17 | 17 | 17.0 |
| 'Floratam' | 26 | 24 | 26 | 27 | 25.8 |

VARIETY DENOMINATION

Origin: Cross pollination performed in greenhouse.
Classification: *Stenotaphrum secundatum* (Walt) Kuntze.
Chromosome number: 18.
Form: Monocot Gramineae.
Growth habit: A perennial plant, with a soloniferous growth habit, which allows it to be propagated vegetatively. A St. Augustinegrass cultivar that exhibits dwarf characteristics manifested in increased density and finer texture, but has a brighter dark green color when compared to other cultivars. This variety is well adapted and well suited for use in the typical area of St. Augustinegrass adaptation.
Establishment rate: Moderate to Moderate/Fast.
Regions of adaptation: Adapted to Florida, Texas and other southern areas where freezing temperatures are not a severe annual problem.
Blade:
*Shape.*—Short, Narrow.
*Length.*—2.3 cm.
*Width.*—0.56 cm.
Leaf color: Dark Green.
Mature plant height: Fifteen (15) to Twenty (20) Centimeters.
Above canopy stolons: Minimal.
Internode length: 3.37 cm.
Internode color: Light Green.
Node width: 2.21 mm.
Soil adaptation: Sandy and heavy soils where adequate moisture is available.
Inflorescence (m/f): Inflorescence is a spike, usually found terminally on a stolon.

REFERENCES

All references cited herein are hereby incorporated by reference in their entireties.

McGuire, R. G., Reporting of objective color measurements. HortScience, 1992. 27(12): pp. 1254–1260.

Mixson, W. C., T. P. Riordan, and V. D. Meier, St. Augustinegrass '6-72-182', in United States Patent Office. 1989, The O. M. Scott & Sons Company; USA.

Arumuganathan, K. and E. D. Earle, Estimation of nuclear DNA content of plants by flow cytometry. Plant Molecular Biology Reporter, 1991. 9(3): pp. 229–233.

Johnson, P. G., T. P. Riordan, and K. Arumuganathan, Ploidy level determinations in buffalograss clones and populations. Crop Science, 1998. 38(2): pp. 478–482.

Leblanc, M. R. and J. N. McCrimmon. Relative ranking as a measure of turfgrass performance under natural tree shade. SNA Research Conference. 1997. Vol. 42.

Busey, Philip. High Impact Turf: Comparative wear tolerance of 25 St. Augustinegrass Cultivars. 1991. Submitted to the American Sod Producers Association.

What is claimed is:

1. A new and distinct perennial St. Augustinegrass cultivar, substantially as herein shown and described, distinguished by its dark green color, improved turfgrass quality, shade tolerance, pest tolerance, dwarf characteristics including short narrow leaf structure, and short average internode length, and vegetative propagation which permits maintenance of a stable genotype.

* * * * *